United States Patent
Oosawa

(10) Patent No.: US 8,023,704 B2
(45) Date of Patent: Sep. 20, 2011

(54) METHOD AND APPARATUS FOR SUPPORTING REPORT CREATION REGARDING IMAGES OF DIAGNOSIS TARGETS, AND RECORDING MEDIUM HAVING PROGRAM FOR SUPPORTING REPORT CREATION REGARDING IMAGES OF DIAGNOSIS TARGETS RECORDED THEREFROM

(75) Inventor: Akira Oosawa, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 1165 days.

(21) Appl. No.: 11/783,519

(22) Filed: Apr. 10, 2007

(65) Prior Publication Data

US 2007/0237377 A1  Oct. 11, 2007

(30) Foreign Application Priority Data

Apr. 10, 2006 (JP) ................................. 2006-107609
Mar. 16, 2007 (JP) ................................. 2007-068562

(51) Int. Cl.
*G06K 9/00* (2006.01)
(52) U.S. Cl. ........ 382/128; 382/305; 382/306; 707/705; 707/736
(58) Field of Classification Search ........................ None
See application file for complete search history.

(56) References Cited

U.S. PATENT DOCUMENTS

| 5,903,664 | A | * | 5/1999 | Hartley et al. | ................. | 382/154 |
| 2003/0105638 | A1 | * | 6/2003 | Taira | ............................. | 704/275 |
| 2004/0003001 | A1 | * | 1/2004 | Shimura | .................... | 707/104.1 |
| 2004/0197018 | A1 | * | 10/2004 | Schultz | ......................... | 382/128 |
| 2004/0243551 | A1 | * | 12/2004 | Boone et al. | ...................... | 707/3 |
| 2005/0163358 | A1 | * | 7/2005 | Moeller | ........................ | 382/128 |
| 2006/0173858 | A1 | * | 8/2006 | Cantlin et al. | .................. | 707/10 |
| 2007/0038611 | A1 | * | 2/2007 | Boone et al. | ...................... | 707/3 |

FOREIGN PATENT DOCUMENTS

JP  2005-160502 A  6/2005

OTHER PUBLICATIONS

Taira et al. ("Automatic Structuring of Radiology Free-Text Reports", 2001, RSNA, vol. 21, No. 1, pp. 237-245).*

* cited by examiner

*Primary Examiner* — Sath V Perungavoor
*Assistant Examiner* — Jason Heidemann
(74) *Attorney, Agent, or Firm* — Sughrue Mion, PLLC

(57) ABSTRACT

Case images and report text models, each of which is a text model derived from a report text of each of the corresponding case images by making at least certain words/phrases within the report text changeable, are stored in association with each other in a case report storage unit. A case image which is similar to a diagnosis target image is retrieved from the case images stored in the case report storage unit by a similar image retrieval unit. Input of a word/phrase corresponding to the diagnosis target image is accepted in a changeable word/phrase section of the report text model by a report creation unit, thereby a report text of the diagnosis target image is created.

8 Claims, 14 Drawing Sheets

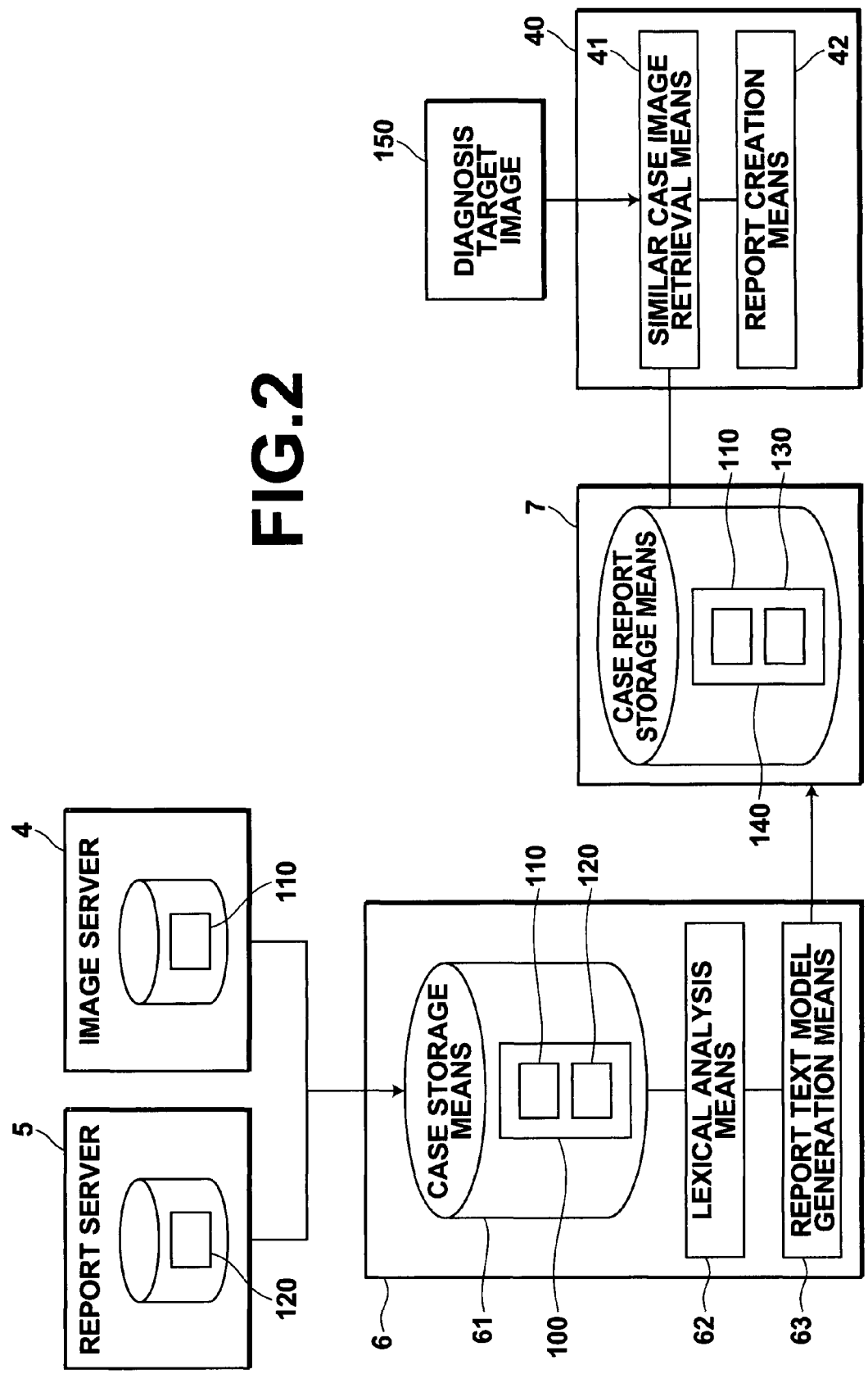

FIG.3

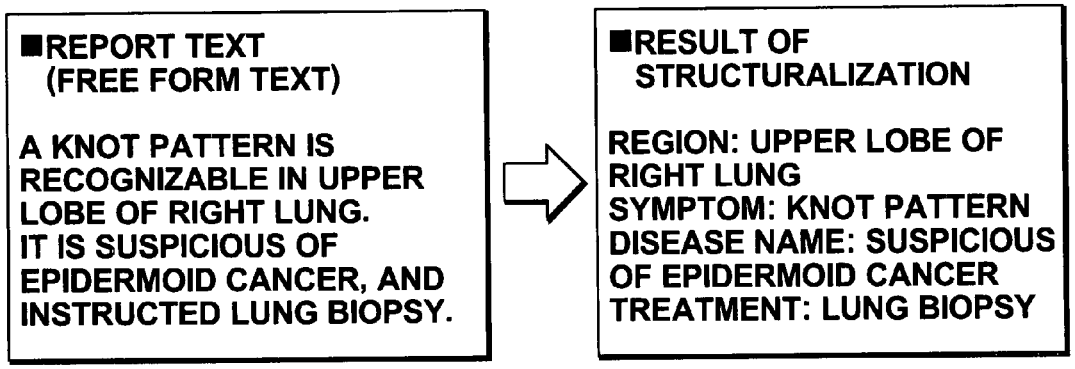

■REPORT TEXT
(FREE FORM TEXT)

A KNOT PATTERN IS RECOGNIZABLE IN UPPER LOBE OF RIGHT LUNG.
IT IS SUSPICIOUS OF EPIDERMOID CANCER, AND INSTRUCTED LUNG BIOPSY.

■RESULT OF STRUCTURALIZATION

REGION: UPPER LOBE OF RIGHT LUNG
SYMPTOM: KNOT PATTERN
DISEASE NAME: SUSPICIOUS OF EPIDERMOID CANCER
TREATMENT: LUNG BIOPSY

FIG.4

| REGION | UPPER LOBE OF RIGHT LUNG ▼ |
| --- | --- |
| SYMPTOM | KNOT PATTERN ▼ |
| DISEASE NAME | SUSPICIOUS OF EPIDERMOID CANCER ▼ |
| TREATMENT | LUNG BIOPSY ▼ |

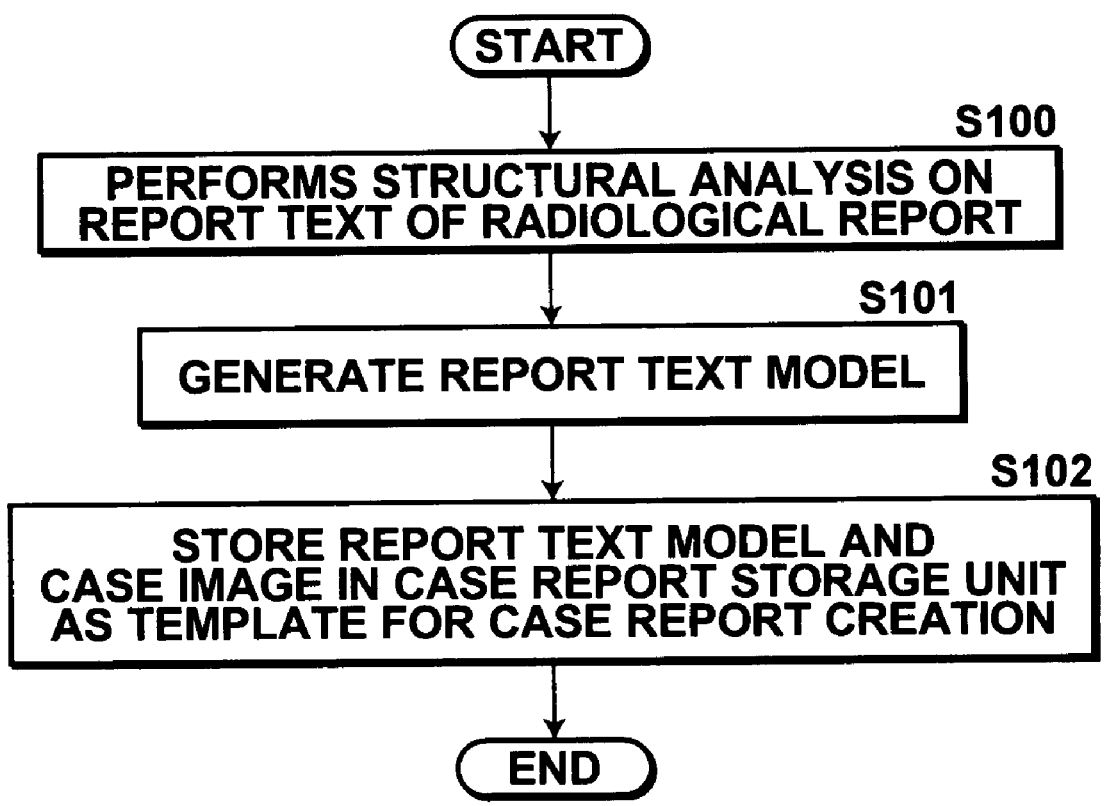

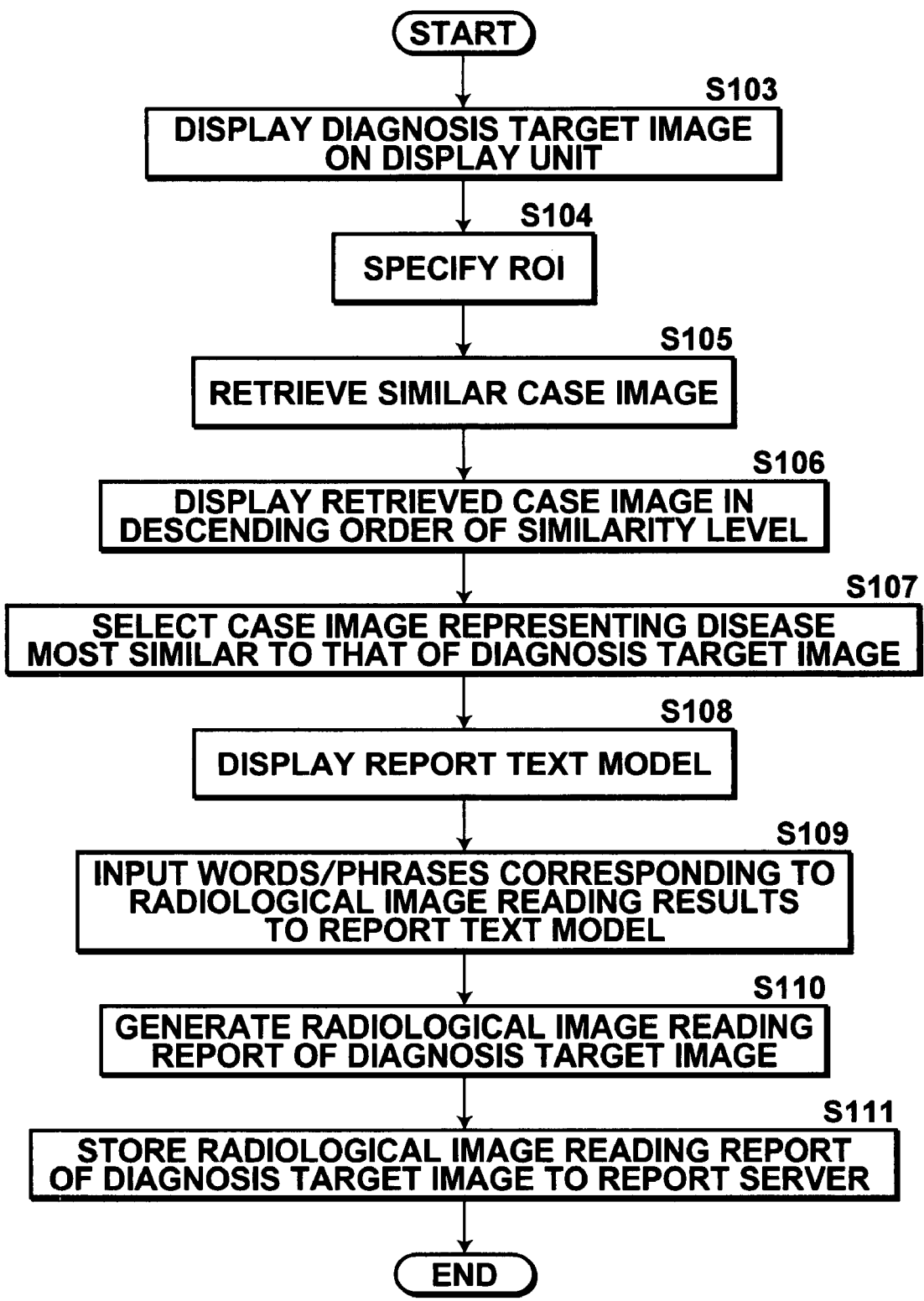

FIG.12
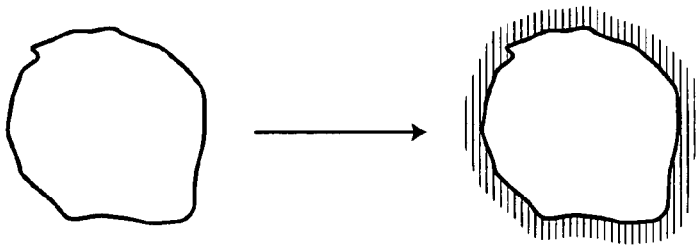
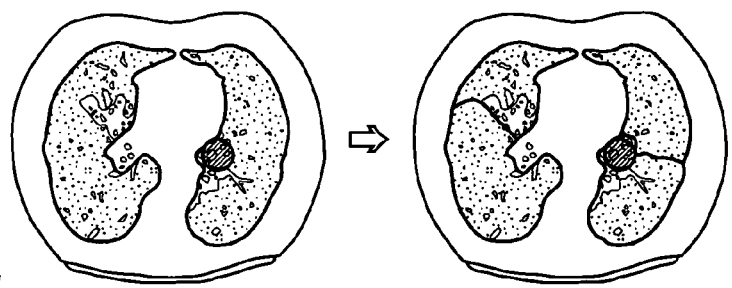
FIG.13B  FIG.13C
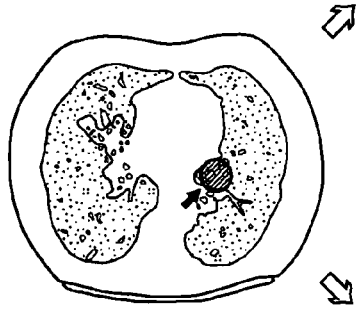
FIG.13A
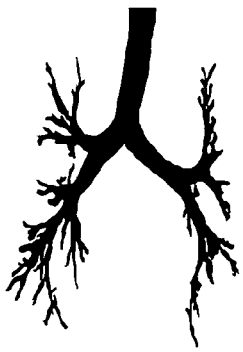  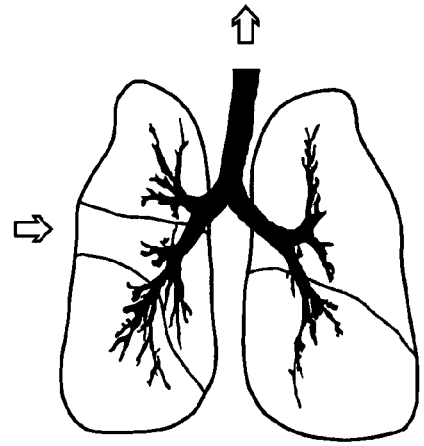
FIG.13D  FIG.13E

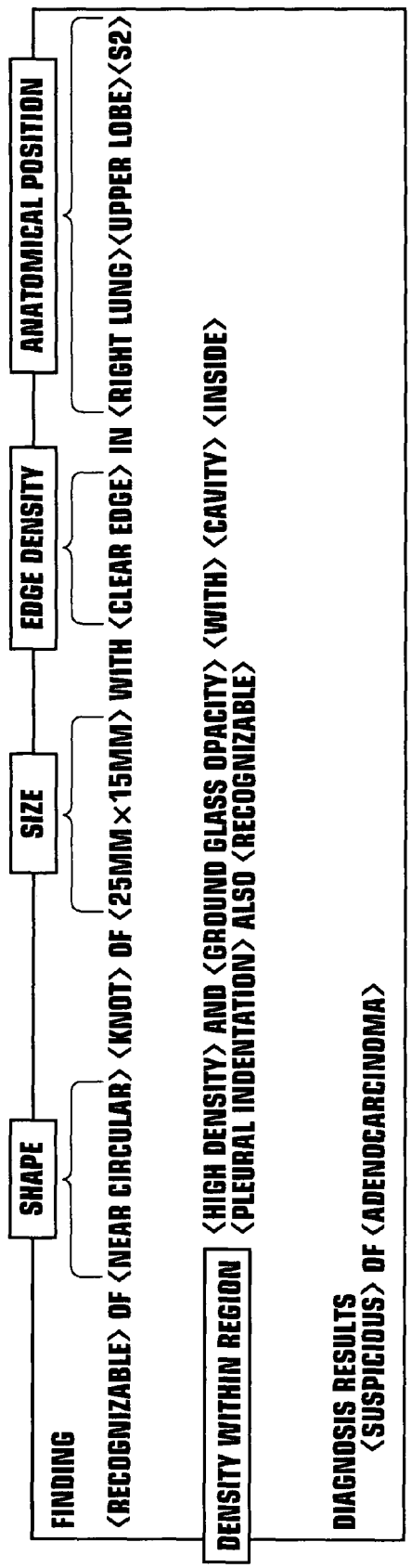

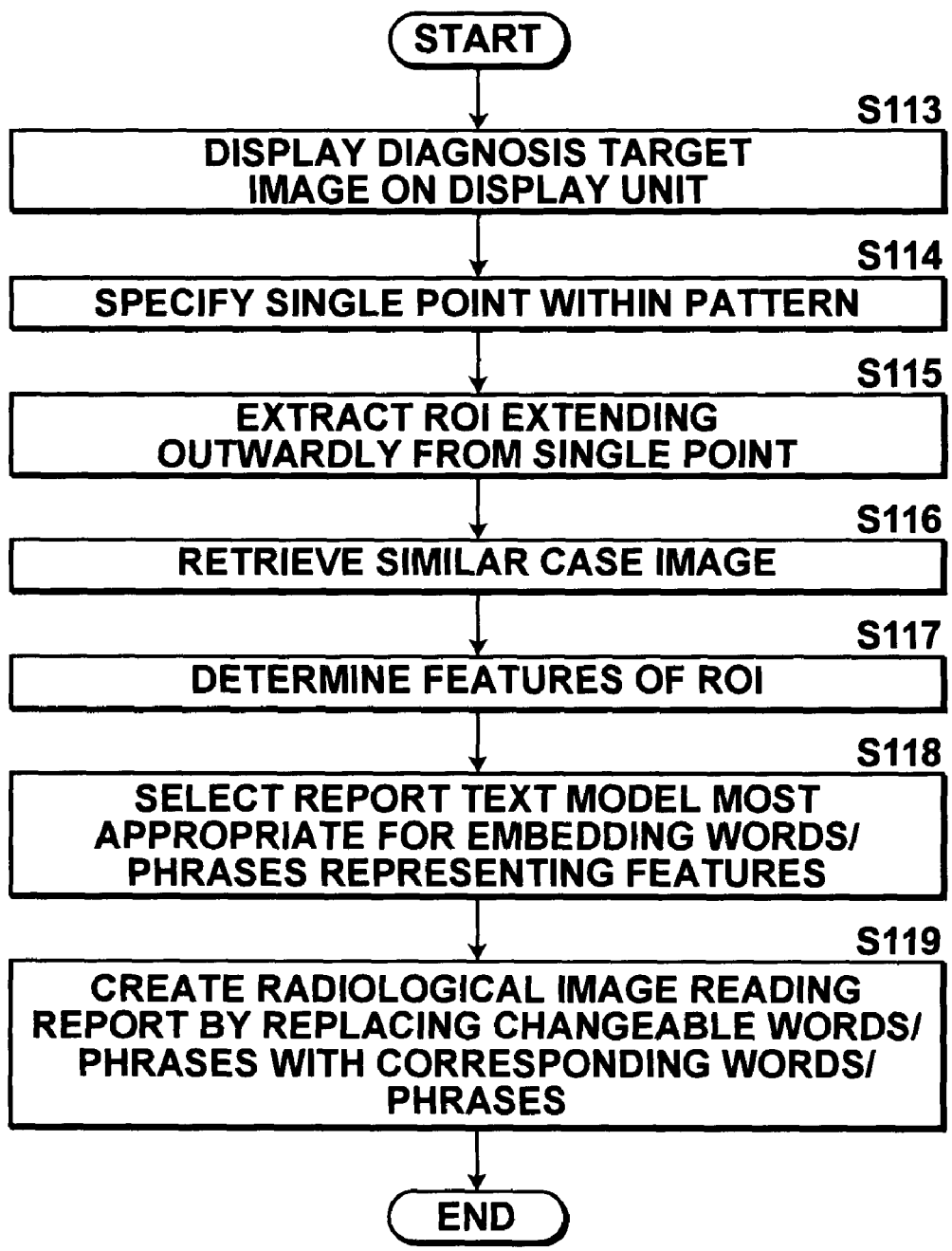

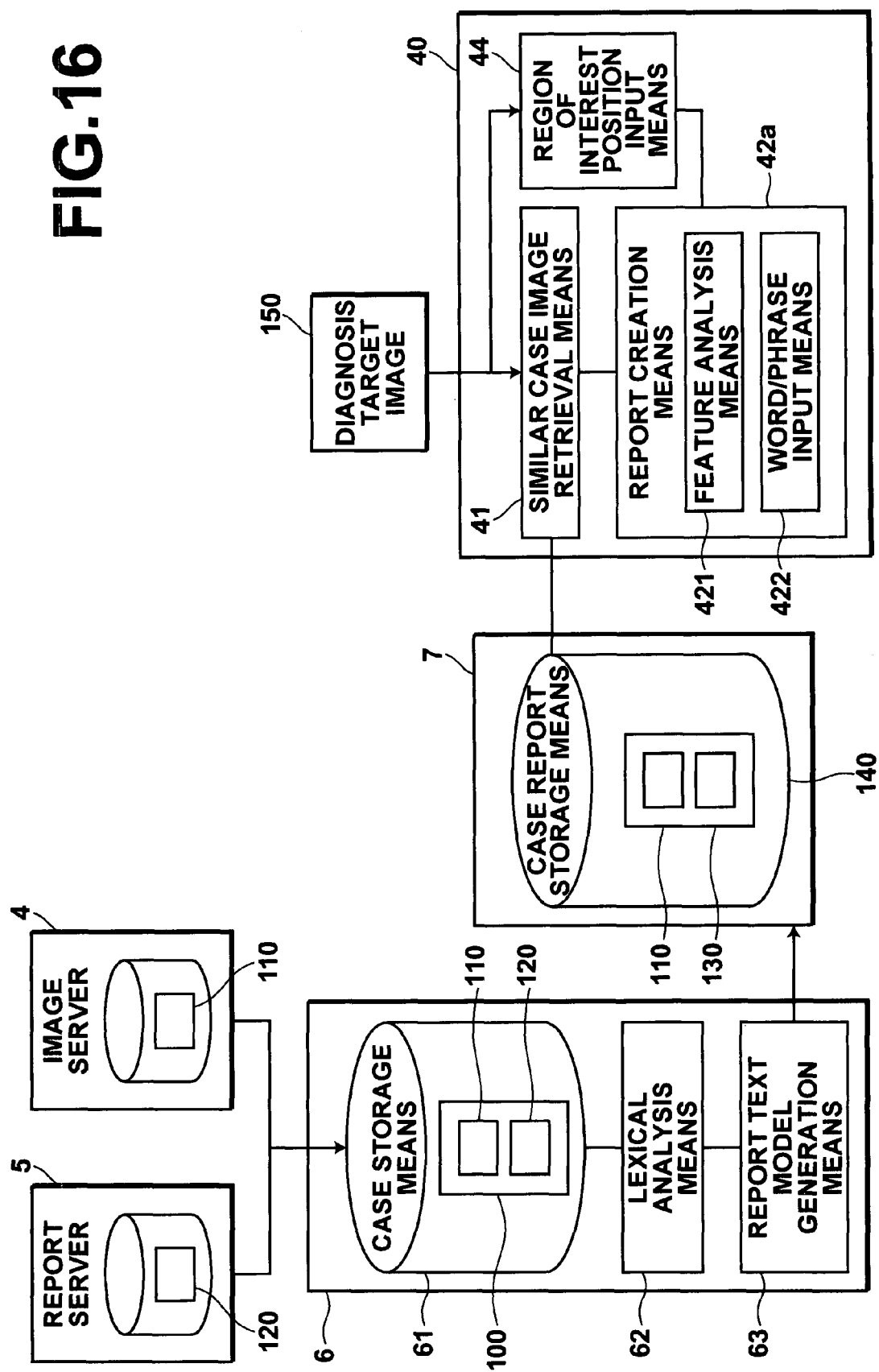

METHOD AND APPARATUS FOR SUPPORTING REPORT CREATION REGARDING IMAGES OF DIAGNOSIS TARGETS, AND RECORDING MEDIUM HAVING PROGRAM FOR SUPPORTING REPORT CREATION REGARDING IMAGES OF DIAGNOSIS TARGETS RECORDED THEREFROM

BACKGROUND OF THE INVENTION

1. Field of the Invention

The present invention relates to a report creation support apparatus and report creation support method for supporting creation of a medical report, and a program therefor.

2. Description of the Related Art

Image diagnosis in which medical staff, including doctors, observes medical images for diagnosis and provides findings, reports, or the like is performed. Digitization of findings or reports using computers, instead of papers, is underway in medical institutions to improve work efficiency and to facilitate the services. In addition, a system that includes electronic reports in a common server, accessible from a plurality of terminals, to allow a plurality of doctors to share the medical reports is proposed.

It is often the case that such reports are entered in free-form texts, and are created while observing displayed medical images. Therefore, it takes time and effort to create the reports. Consequently, a method for reducing the burden of creating the reports is proposed as described, for example, in Japanese Unexamined Patent Publication No. 2005-160502. In the method, sample texts for describing medical images are stored in association with the accompanying information, including the types of imaging devices used for obtaining the medical images, regions, examination dates and times, patient identifications, and the like, then a sample text is automatically selected from these samples based on the accompanying information, and the features of a lesion in a medical image are applied to the selected sample text to create a report of the medical image. Further, the method allows created sample texts and reports to be edited, and use of past reports of patients.

The method described above, however, uses past reports of the same patient, so that the report needs to be modified largely according to the progression of the lesion. Further, the past reports of the same patient are not always useful, depending on the progression of the disease.

In the mean time, if the features of lesions appearing on medical images are similar to each other, it is often the case that similar reports are created. Further, when performing diagnosis, it is often the case that a similar image is retrieved from the medical images obtained in the past, and a report for the patient is provided by referring to the case of the retrieved image.

SUMMARY OF THE INVENTION

It is an object of the present invention, therefore, to provide a method for readily creating a report of a diagnosis target image of a patient by retrieving a case similar to the case of the diagnosis target image from the past cases and using the report of the similar case.

The report creation support apparatus of the present invention is an apparatus, including:

a case report storage means for storing a plurality of different case images, each with a report text model associated therewith, the report text model being a text model derived from a report text of the corresponding case image by making at least certain words/phrases included therein changeable;

a similar case image retrieval means for retrieving a case image which is similar to a diagnosis target image from the case images stored in the case report storage means; and a report creation means for creating a report text of the diagnosis target image by accepting input of a word/phrase appropriate for the diagnosis target image in a changeable word/phrase section of the report text model corresponding to the case image which is similar to the diagnosis target image retrieved by the similar case image retrieval means.

The program of the present invention is a program for causing a computer to function as:

a similar case image retrieval means for retrieving a case image which is similar to a diagnosis target image from a plurality of different case images, each stored with a report text model associated therewith in a case report storage means, the report text model being a text model derived from a report text of the corresponding case image by making at least certain words/phrases included therein changeable; and a report creation means for creating a report text of the diagnosis target image by accepting input of a word/phrase appropriate for the diagnosis target image in a changeable word/phrase section of the report text model corresponding to the case image which is similar to the diagnosis target image retrieved by the similar case image retrieval means.

The "report text of the corresponding case image" includes contents corresponding to the image of the case image. For example, it is a report of a case image created by a doctor or the like through radiological reading, or the like.

The referent of "word/phrase" as used herein means a character or a character string in a text, which is a minimum unit having a meaning in the text.

Further, the referent of "making at least certain words/phrases changeable" as used herein means replacing certain characters or character strings in a report text with other characters or character strings. The changeable word/phrase section may be replaced by a blank, instead of a character, such as "kanji", Japanese ideographical character, or "hiragana", Japanese phonetic character.

Preferably, the report text model is a text model derived from the report text of the case image by extracting words/phrases therefrom describing features of the case of the case image by performing a lexical analysis thereon and making at least certain words/phrases of the extracted words/phrases changeable.

The referent of "lexical analysis" as used herein means dividing a series of characters into a minimum unit of word/phrase having a meaning.

The referent of "words/phrases describing features of the case of the case image" as used herein means, for example, words/phrases describing a region of the case image, symptom, disease name, treatment given to the subject of the case image, features of a region of interest, position of a region of interest, and the like.

Further, the report creation means may be a means including: a feature analysis means for analyzing a feature of a region of interest within the diagnosis target image; and a word/phrase input means for accepting a word/phrase describing the analyzed feature to replace a word/phrase to be replaced therewith among changeable words/phrases included in the report text model.

The referent of "a word/phrase describing the analyzed feature" means a character string describing the analyzed feature of the region of interest.

Preferably, the feature analysis means is a means for analyzing at least one of the features related to the shape of a region of interest, size of the region of interest, density within the region of interest, density of an edge portion of the region of interest, and anatomical position of the region of interest.

Further, the report creation support apparatus may further include a region of interest position input means for accepting input of a position of a region of interest on the diagnosis target image; and the feature analysis means may be a means for analyzing a feature of the region of interest located in the inputted position on the diagnosis target image.

Still further, the report creation support apparatus may further include an extraction means for extracting a region of interest from the diagnosis target image; and the feature analysis means may be a means for analyzing a feature of the extracted region of interest.

Further, the extraction means may be a means for accepting input specifying a single point on the diagnosis target image, and extracting a region of interest located around the single point.

The report creation support method of the present invention is a method, including:

a lexical analysis step for performing a lexical analysis on a report text stored in association with each of a plurality of different case images in a case storage means;

a report text generation step for generating a report text model by extracting words/phrases describing features of the case of the case image from the words/phrases obtained through the lexical analysis, and making at least certain words/phrases of the extracted words/phrases changeable;

a case report storing step for storing the generated report text model in association with each of the plurality of corresponding case images in a case report storage means;

a similar case retrieval step for retrieving a case image which is similar to a diagnosis target image from the case images stored in the case report storage means; and a report text model output step for outputting a report text model corresponding to the retrieved case image which is similar to the diagnosis target image.

The referent of "outputting a report text model" as used herein means to make the report text model ready for use by, for example, displaying it on a display unit.

In the present invention, case images and report text models, each corresponding to each case image, are stored in association with each other, then a case image similar to a diagnosis target image is retrieved, and a report of the diagnosis target image is created using the report text model of the retrieved case image. This allows a report text well describing the features of the diagnosis target image to be created readily by retrieving and using a report text model appropriate for the features of the diagnosis target image.

Further, provision of report text models by performing the lexical analysis on report texts of case images created in the past, and making certain words/phrases changeable, many different diagnosis text patterns appropriate for respective case images may be provided.

By analyzing features of a ROI within a diagnosis target image and replacing changeable words/phrases included in a report text model with words/phrases describing the analyzed features, an accurate report may be created automatically without requiring manual input of a doctor performing radiological image reading.

Further, by analyzing features related to the shape, size, density, and edge density of a ROI, and anatomical position of the ROI, useful information for the diagnosis of a tumor, and the like, may be inputted to the report.

Still further, if a configuration is adopted in which input of a position of a ROI on a diagnosis target image is accepted, and features of the ROI located in the inputted position are analyzed, a report of the ROI being observed by a doctor performing radiological image reading may be created automatically.

Further, if an extraction means for extracting a ROI from a diagnosis target image is provided, a report of the diagnosis target image may be created automatically without requiring a doctor performing radiological image reading to specify the ROI.

Still further, if a configuration is adopted in which input specifying a single point on a diagnosis target image is accepted, and a ROI located around the single point is extracted, a report of the region being observed may be created, and at the same time a ROI may be extracted accurately and an accurate report may be created automatically without specifying the ROI accurately.

BRIEF DESCRIPTION OF THE DRAWINGS

FIG. 2 is a block diagram of a report text model generation unit and report creation support apparatus according to a first embodiment, illustrating the schematic construction thereof.

FIG. 3 illustrates the structuralization of a report text.

FIG. 4 illustrates an example input method of sample words/phrases to the report text.

FIG. 5 is a flowchart illustrating a flow for generating a report text model (first flowchart).

FIG. 6 is a flowchart illustrating a flow for creating a radiological report of a diagnosis target image using the report text model.

FIG. 12 illustrates a ROI and a surrounding area thereof.

FIGS. 13A to 13E illustrate a method for analyzing an anatomical position in a chest image.

FIG. 14 illustrates an example report text model.

FIG. 15 is a flowchart illustrating a flow for creating a radiological report of a diagnosis target image using the report text model (second flowchart).

FIG. 16 is a block diagram of a report text model generation unit according to the second embodiment and another report creation support apparatus, illustrating the schematic construction thereof.

DESCRIPTION OF THE PREFERRED EMBODIMENTS

Figure 1:
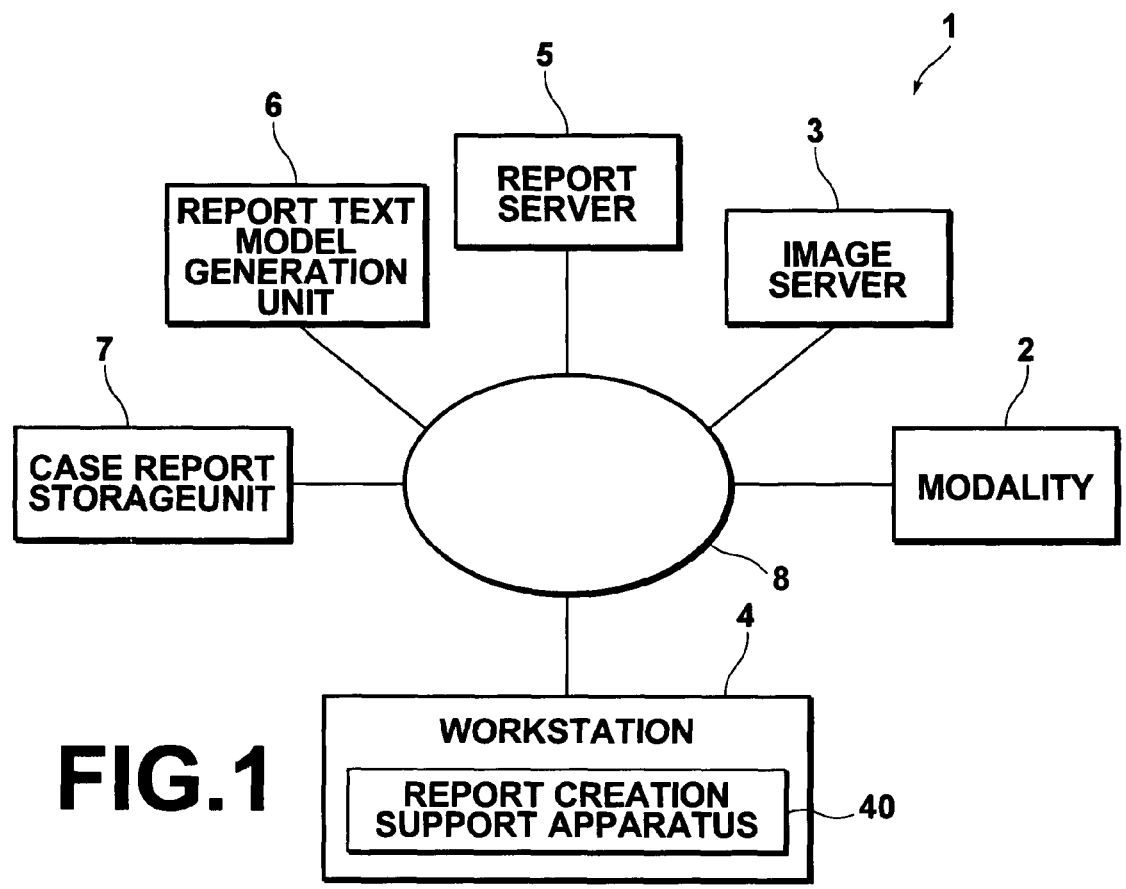
FIG. 1 is a block diagram of a medical system, illustrating the schematic construction thereof.

Hereinafter, exemplary embodiments of the present invention will be described with reference to the accompanying drawings. FIG. 1 is a block diagram of a medical system including the report creation support apparatus according to a first embodiment of the present invention, illustrating the schematic construction thereof. As illustrated, the medical system 1 according to the present embodiment includes: a modality 2 for obtaining medical images; an image server 3 for storing medical images obtained by imaging diseased areas of subjects; a workstation 4 for doctors to perform radiological image reading; a report server 5 for storing reports created by the doctors through radiological reading of images displayed on the screen of the workstation 4; a report text model generation unit 6 for generating report text models; a case report storage unit 7 for storing the report text models; and a network 8.

The modality 2 is a device or a system for recording medical images of patients as digital data, such as CR (Computed Radiography), MRI (Magnetic Resonance Imaging), US (Ultrasound Imaging), or the like.

The image server 3 receives a large amount of medical images from each of the modalities 2 installed in the radiological department and the like through the network 8, and stores them in a DICOM compliant format together with patient information, date and time of recording, information of the modality used, and the like. The image server 3 includes database management software, and is capable of retrieving medical images stored therein using various types of information accompanying the medical images.

The workstation 4 has a function to read out a target medical image for performing radiological image reading from among the medical images stored in the image server 3 through the network 8, and to display the target medical image on the screen of the image display unit. Preferably, the workstation includes a high definition display unit, such as CRT or the like.

Further, the workstation 4 includes a report creation support program, and may also serve as a report creation support apparatus 40.

The report server 5 stores radiological image reading results performed by doctors at the workstation 4, as radiological reports.

As illustrated in FIG. 2, the report text model generation unit 6 includes: a case storage means 61 for storing a plurality of sets of case data 100; a lexical analysis means 62 for performing lexical analysis on the report text included in the radiological reports; and a report text model generation means 63 for generating case report creation templates 140 by extracting words/phrases from among the lexically analyzed report texts describing features of the cases of case images and generating report text models by making the extracted words/phrases changeable.

The case data 100 includes a case image 110, a radiological report 120 of the case image 110, and the like. The case image 110 of the case data 100 is selected from the medical images stored in the image server 3, and a radiological report 120 corresponding to the selected medical image 110 is fetched from the report server 5. Preferably, the case data 100 further includes positional information of a ROI (Region of Interest) on the case image 110 where a disease is present.

The report text model 130 is a report text model which will turn into an appropriate report text for a diagnosis target image 150 by changing only certain words/phrases, and thereby a report text of the diagnosis target image is created easily. There are many different writing patterns for report text. Therefore, a text model, which allows only words/phrases to be changed in order to make it appropriate for the diagnosis target image 150 based on a radiological reports 120 of the case data 100 generated in the past and stored in the case storage means 61, is used as the report text model 130.

The lexical analysis means 62 performs a structural analysis on a report text of the radiological report 120 entered in free-form text though a text mining approach. First, the report text is divided into words through a morphological analysis, then extracted words are checked with a medical dictionary or the like to allocate the meaning to the segments and words, and the words/phrases describing features of the case of the case image, such as the words/phrases in the finding description section and diagnosis description section, are extracted. For more detail information, reference is made to: a literature by Yamagishi et al., Symposium Proceedings for 24th annual meeting of JAMIT (The Japanese Society of Medical Imaging Technology), pp. 5-6, Jul. 2005; a literature by Imai and Onogi, Symposium Proceedings for 24th annual meeting of JCMI (Japan Association of Medical Informatics), November 2004; a literature by Imai and Onogi, Symposium Proceedings for 23rd annual meeting of JCMI, November 2003; a literature "Extracting Diagnosis from Japanese Radiological Report" by Imai and Onogi, Symposium Proceedings of AMIA 2003, p. 873; and the like.

The report text model generation means 63 generates a report text model 130 by selecting certain words/phrases to be made changeable from the words/phrases included in the phrase-analyzed report text describing the features of the case of the case image 110, and combines the generated report text model with the case image 110 of the radiological report 120, the source report of the model, thereby a case report creation template 140 is generated. Preferably, the case report creation template 140 also includes location information of a ROI in the case image 110. The created case report creation template 140 is stored in a case report storage means 43. It is preferable that case report creation templates 140 be provided as many as possible in order to cover various cases.

For example, words/phrases describing the features of the case of the case report 110, such as "upper lobe of right lung", description of the region, "knot shadow", description of the symptom, "squamous cancer", description of the disease name, and "lung biopsy", description of the treatment, are extracted from a report of free-form text illustrated in FIG. 3 by performing a structural analysis, and the extracted words/phrases are made changeable. The report text model 130 may also be a report text model with such changeable words and phrases replaced by blanks.

The case report storage unit (case report storage means) 7 also includes multitudes of case report creation templates 140, each constituted by a case image 110 and a report text model 130 of the case image 110 generated by the report text model generation means 63.

The report creation support apparatus 40 includes: a similar case image retrieval means 41 for retrieving the case image 110 of a case report creation template 140, which is similar to a diagnosis target image 150; and a report creation means 42 for creating a report of the diagnosis target image 150 using the report text model 130 of the case report creation template 140 corresponding to the retrieved case image 110.

The similar case image retrieval means 41 retrieves a case image 110, which is similar to a diagnosis target image 150, from case images 110 of case report creation templates 140 stored in the case report storage means 7. More specifically, several case images 110 are retrieved based on the similarity level in the features between the ROI of a case image 110 and the ROI of the diagnosis target image 150 in descending order. The similarity level may be obtained using (a) distance in a feature amount space of the feature amounts obtained from the ROI of the diagnosis target image 150 and the ROI of a case image 110, (b) RMS (root mean square) of the ROI of the diagnosis target image 150 and the RMS of the ROI of a case image 110, (c) cross-correlation between the ROI of the diagnosis target image 150 and the ROI of a case image, (d) device learned through a neural network processor the like as described, for example, a literature "Investigation of new psychophysical measures", Medical Physics, Vol. 30, No. 10, October 2003, pp. 2584-2593.

The report creation means 42 displays the report text model 130 included in a case report creation template 140 of a case image 110, which is similar to the diagnosis target image 150, on a display unit to allow entry of the report of the diagnosis target image 150. The report text model 130 is displayed such that the words/phrases describing the features of the case are allowed to be changed so that the report text model 130 is modified to the report corresponding to the diagnosis target image 150. For example, frames containing words/phrases describing the region, symptom, disease name, and treatment are displayed, and if one of the triangular marks on the side of the frames is clicked, a list of words/phrases to be entered into the frame is displayed as a pull-down menu to allow the selection of a word/phrase from the list, as illustrated in FIG. 4.

Generation of a report text model and a flow for creating a report using the generated report text model will now be described based on the flowchart illustrated in FIG. 5.

The report text model generation means 6 performs a structural analysis on a radiological report 120, provided in free-form text, of case data 100 stored in the case storage means 61 by the lexical analysis means 62 using a text mining approach (S100), and extracts words/phrases describing the features of the case of the case image 110 from the lexically analyzed report text by the report text model generation means 63 to generate a report text model 130 in which certain extracted words/phrases to be made changeable are selected (S101). The generated report text model and the case image 110 corresponding to the radiological report 120, which is the source report of the model, are stored in the case report storage unit 7 as a case report creation template 140 (S102).

A flow for generating a radiological report of a diagnosis target image in the report creation support apparatus using a case report creation template generated in the manner as described above will now be described based on the flowchart illustrated in FIG. 6.

First, a doctor performing radiological image reading reads out a diagnosis target image 150 from the image server 3 and displays on the display unit of the workstation 4 (S103). Then, the doctor indicates a ROI on the displayed diagnosis target image 150 by encircling it using a mouse or the like (S104). Then, case images 110 with ROIs similar to the ROI indicated on the diagnosis target image 150, which may be identified by ROI position information of the case report creation templates 140 stored in the case report storage unit 7, are retrieved by the similar case image retrieval means 41 (S105).

Figure 7:
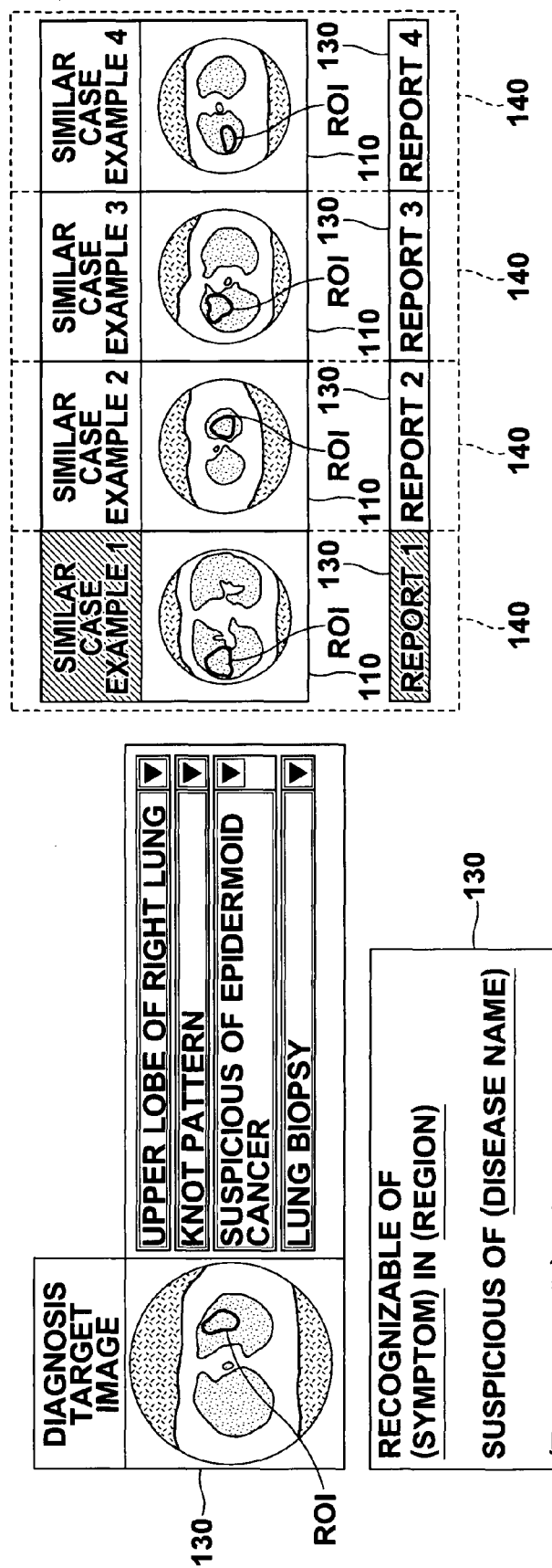
FIG. 7 illustrates an example display screen for selecting a report text model of a case image which is similar to the diagnosis target image.

The retrieved case images 110 are displayed on the report creation means 42 in descending order of the similarity level (S106). Further, the ROIs on the displayed case images are encircled or the like using the ROI position information included in the case report creation template 140, so that they are readily identified as illustrated in FIG. 7.

Then, when a case image 110 representing a disease which seems most similar to that of the diagnosis target image 150 is selected from the displayed case images 110 of the case report creation templates 140 by the doctor (S107), the report text model 130 is extracted from the case report creation template 140 of the selected case image 110 and displayed on the display unit by the report creation means 42 (S108). In FIG. 7, the case image 110 indicated as "Similar Case Example 1" is selected, and the display of the selected "Similar Case Example 1" and "Report text 1", which is the report text model 130 of the similar case example 1, are highlighted. Further, the FIG. 7 illustrates that the model 130 of the "Report text 1" is displayed below the diagnosis target image 150. When words/phrases corresponding to the reading results of the diagnosis target image 150 are entered by the doctor by selecting from the pull-down menu after observing the diagnosis target image 150 (S109), a radiological report 120 of the diagnosis target image 150 is created from the report text model 130 and inputted words/phrases through the report creation means 42 (S110). The created radiological report 120 of the diagnosis target image 150 is stored in the report server 5 (S111).

As described in detail, the use of report text models generated from radiological reports corresponding to images obtained in the past allows appropriate reports for many different diagnosis target images to be created easily.

So far, the description has been made of a case where the structure of a radiological report is analyzed through the text mining approach. But, the structural analysis may be performed manually to generate a report text model.

Next, a second embodiment will be described. In the first embodiment, the description has been made of a case where a ROI is encircled and extracted by the doctor performing radiological image reading through a mouse or the like to retrieve similar case images. But, in the present embodiment, description will be made of a case where a ROI is extracted using CAD function to retrieve similar case images. Further, in the first embodiment, the description has been made of a case where the locations of the ROIs are displayed using the position information of the ROIs of the case images included in advance in the case report creation templates, when displaying case images similar to the diagnosis target image. But, in the present embodiment, when displaying similar case images, ROIs are automatically extracted using CAD function and displayed. Further, in the present embodiment, a report in which a changeable word/phrase in a report text model is automatically replaced using a result of CAD is generated. In the present embodiment, elements identical to those used in the first embodiment will be given the same reference numerals, and will not be elaborated upon further here.

Figure 8:
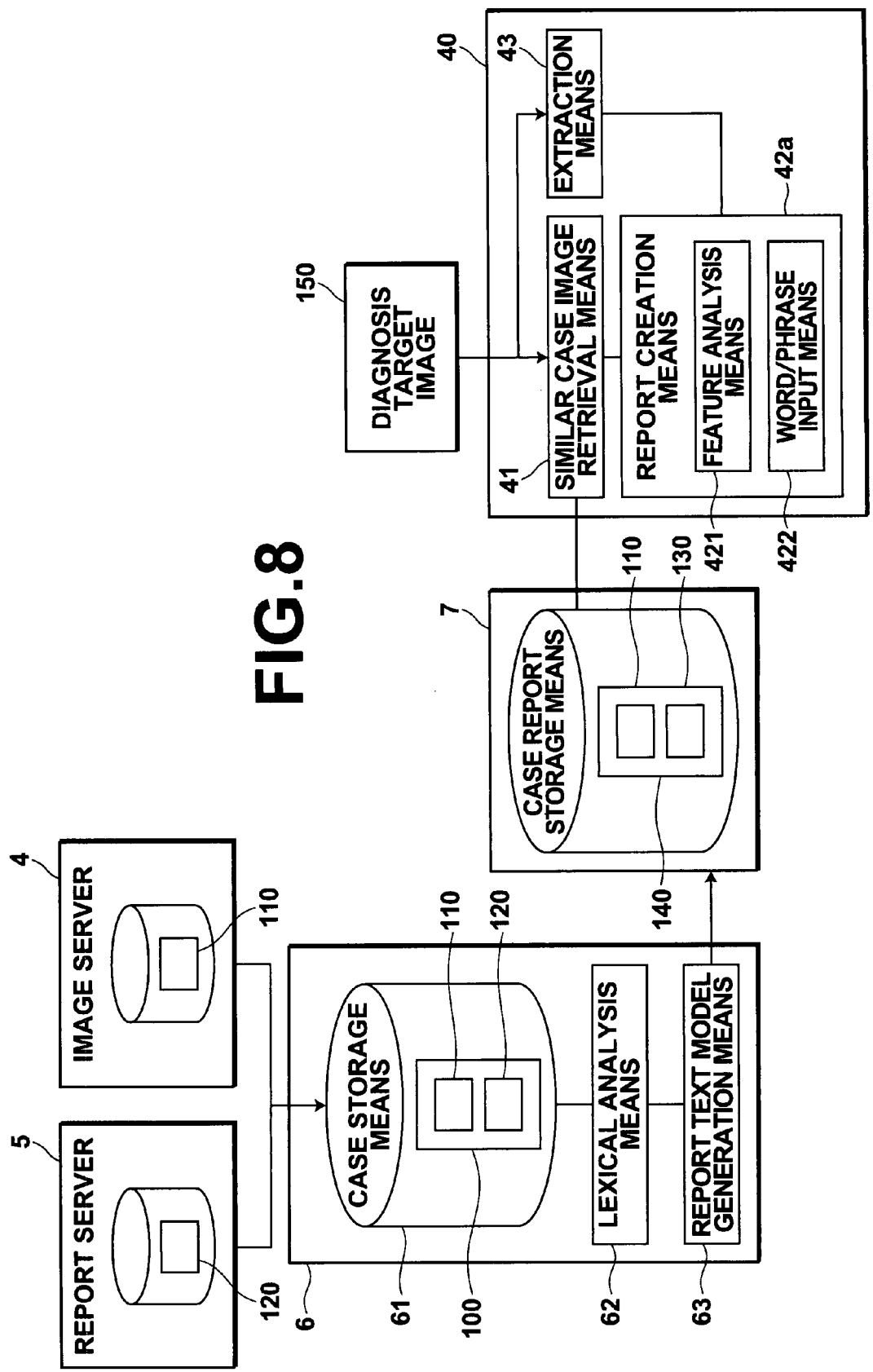
FIG. 8 is a block diagram of a report text model generation unit and report creation support apparatus according to a second embodiment, illustrating the schematic construction thereof.

The schematic configuration of a medical system including a report creation support apparatus according to the present embodiment is similar to that of the first embodiment, but differs in the report creation support apparatus. As illustrated in FIG. 8, the report creation support apparatus 40a includes: the similar case image retrieval means 41; an extraction means 43 for extracting a ROI from a diagnosis target image; and a report creation means 42a for creating a report of the diagnosis target image 150.

The report creation means 42a includes: a feature analysis means 421 for analyzing features of a ROI extracted by the extraction means 43; and a word/phrase input means 422 for accepting input of a word/phrase describing the analyzed feature to replace a word/phrase to be replaced therewith among changeable words/phrases included in the report text model.

When a point within a ROI of a diagnosis target image 150 is specified by a doctor performing radiological image reading, the extraction means 43 extract the ROI, such as a tumor region, by searching a surrounding area of the point. Preferably, the specified point is close to the center of the tumor region.

Figure 9:
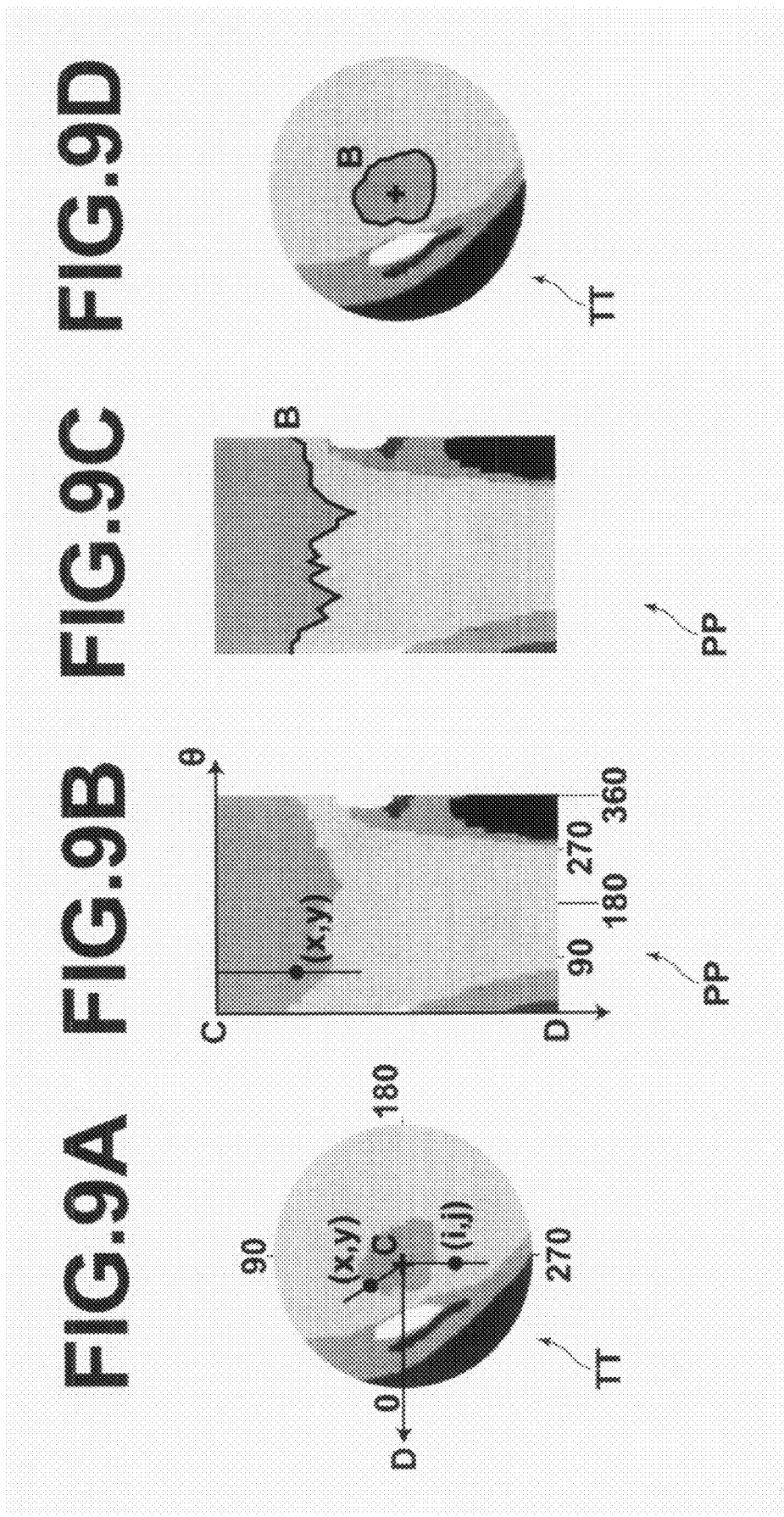
FIGS. 9A to 9D illustrate a method for automatically extracting a ROI.
Figure 10:
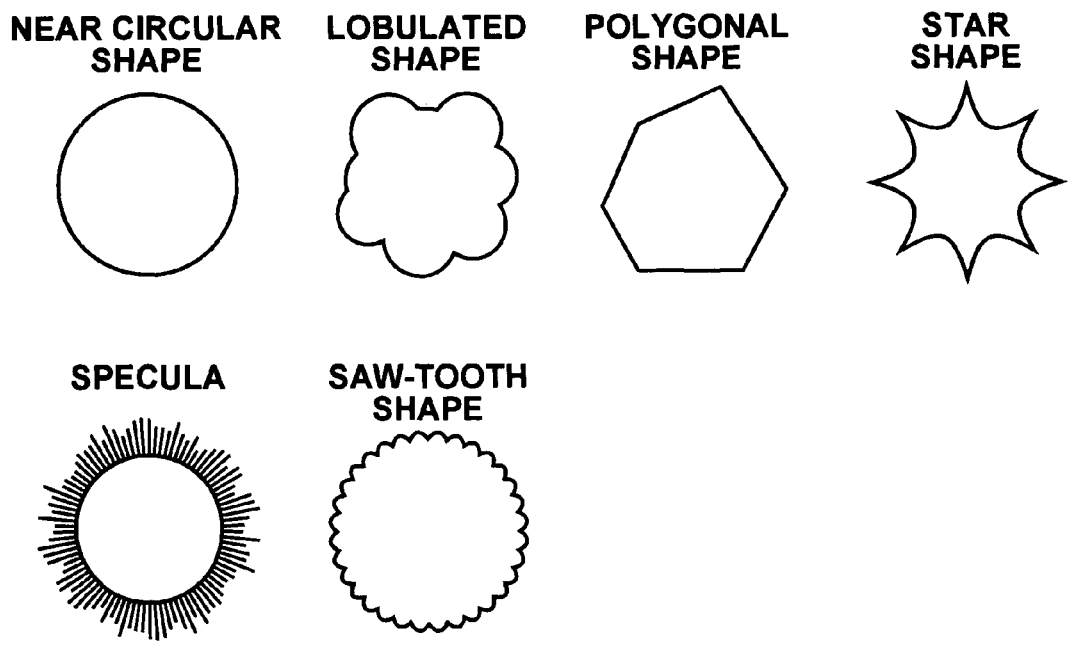
FIG. 10 illustrates example classification of shapes.

First, a region having a certain radius sufficient to include a tumor region centered on a specified point C is determined as a discrimination region TT, as illustrated in FIG. 9A. Then, the image of the discrimination region TT like that illustrated in FIG. 9A is transformed into a discrimination image PP, which is the image of the discrimination region TT developed on a polar coordinate plane represented by the distance from the point C and angle θ formed with a predetermined straight line passing through the point C. For example, a determination is made whether or not each pixel within the discrimination region is a contour of the tumor region, using a polar coordinate image illustrated in FIG. 9B obtained by performing polar coordinate transformation of the image illustrated in FIG. 9A with the clockwise direction with reference to the line segment C-D in the radial direction of the image as angle θ.

Based on a feature amount L extracted from luminance information within a one-dimensional luminance profile passing through each pixel (x, y) within the discrimination region and the point C, an evaluation value S that indicates whether or not each pixel within the discrimination region is a pixel representing a contour.

The one-dimensional luminance profile passing through each pixel (x, y) and the point C changes rapidly in luminance value before and after the contour of the tumor region. Thus, feature amounts are extracted from luminance values and a discriminator using the luminance values may be generated. Based on the result obtained by the discriminator, an image (x, y) forming a contour like that as illustrated by a bold line in FIG. 9C is obtained. Then, the discrimination region PP represented by the polar coordinate system is inversely transformed into an ordinary coordinate system, and the contour of the discrimination region TT on the image is determined as illustrated in FIG. 9D. Thereafter, the region surrounded by the contour is extracted as the tumor region (i.e., ROI).

Alternatively, the ROI may be extracted using a region separation technique as described, for example, in a literature "Volu-metric measurements of pulmonary nodules at multi-row detector CT: in vivo reproducibility" by Wormanns D et al., Eur Radiol, 2004; 14(I); pp. 86-92.

The feature analysis means 421 analyzes features of the ROI extracted by the extraction means 43.

If the ROI is an abnormal tissue pattern, such as a tumor or a pulmonary nodule, appearing on a lung field, it has features related to shape, size, edge, and density within the region. Further, the anatomical position where an abnormal pattern appears may also be considered to be one of the features. Therefore, an analysis of the ROI is performed to obtain features in shape, size, density within the ROI, density in the edge of the ROI, anatomical position of the ROI, and the like.

(1) Shape Features

Shapes of abnormal patterns may be classified into near circular shape, lobulated shape, polygonal shape, star shape, specula, saw-tooth shape, and irregular shape. (For more detail information, reference is made to, for example, a literature by Iwano, et al., JRC2006.)

These shapes may be classified by the circularity (ratio between the perimeter and area) shown in Formula 1 below, and second moment (square sum of the distance between the gravity center of a nodule and each pixel point within the nodule normalized by square of the area) shown in Formula 2 below.

$$\text{Circularity} = \frac{4\pi \text{Area}}{\text{Perimeter}^2} \quad (1)$$

$$\text{2nd moment} = \frac{\sum_R \{(x-xg)^2 + (y-yg)^2\} f(x,y)}{\text{Area}^2} \quad (2)$$

where, xg, yg: barycentric position of nodule,
x, y: pixel position within nodule,
f(x,y): pixel value at pixel position within nodule.

Figure 11:
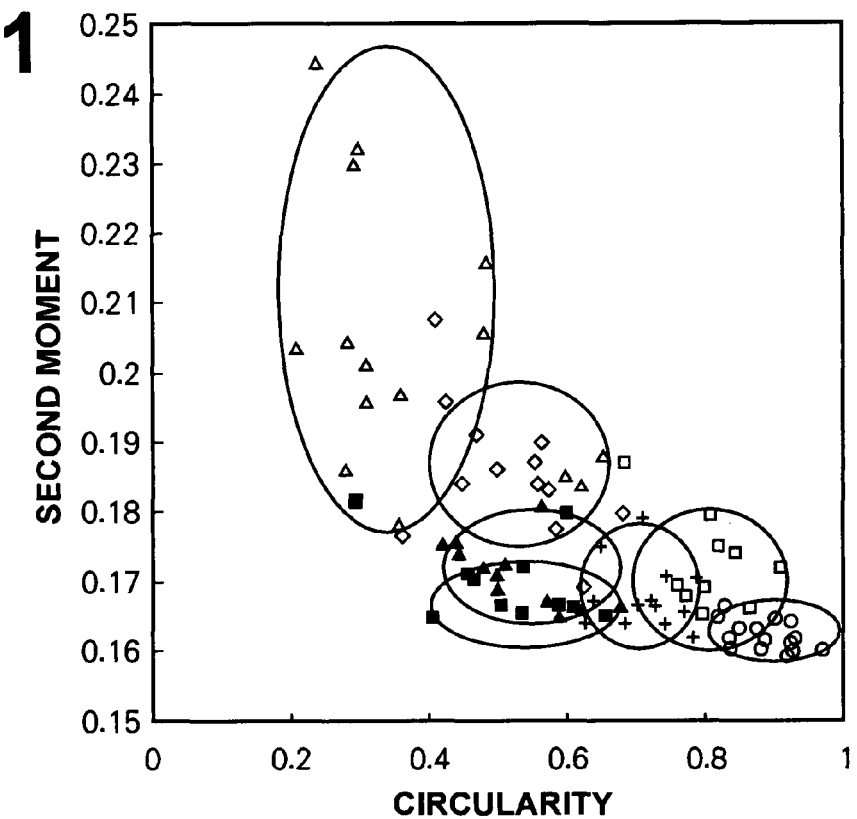
FIG. 11 illustrates the relationship among the classification of shapes, second moment, and circularity.

The circularity and second moment are distributed in the manner as illustrated in FIG. 11, and near circular shapes, lobulated shapes, polygonal shapes, star shapes, speculae, saw-tooth shapes, and irregular shapes (not belonging to any preceding types) are classified into the respective areas encircled by ellipsoids. Thus, a discriminator that outputs a shape type by receiving feature amounts, such as the circularity, second moment, and the like, may be realized using an existing nonlinear discrimination method, design discrimination method, or the like.

(2) Size Features

The size of an abnormal pattern is represented by the area, volume, length of long axis, length of short axis, and the like, which may be automatically measured from a ROI extracted by the extraction means 43.

(3) Density Features within ROI

Abnormal patterns are classified into pure GGO (ground glass opacity), mixed GGO (ground glass opacity and high density), and solid (high density) depending on the density, which may be discriminated by an existing nonlinear discrimination method, design discrimination method, or the like, using the average value, deviation, maximum value, and minimum value of the density within the ROI extracted by the extraction means 43 as feature amounts.

Further, from the density values, ROIs may be classified into those that include calcification or a cavity, and those not including any calcification or cavity. If a maximum density value of a ROI is greater than or equal to a certain threshold value (e.g., CT value of 500), the ROI is determined to include calcification. If the minimum density value of a ROI is smaller than or equal to a certain threshold value (e.g., CT value of 500), the ROI is determined to include a cavity.

(4) Density Features in Edge Portion of ROI

The edge portions of abnormal patterns may be classified into those which are clear and those which are not clear. Determination of whether the edge portion is clear or unclear may be made using the difference in density between the inside and outside of a ROI extracted by the extraction means 43. For a ROI with the contour indicated by a bold line in FIG. 12, the difference in density between the inside region (inside of the contour) and the surrounding region (outside of the contour, shaded area) is obtained from the density values thereof using Formula 3 below.

Density Difference=[average density value (surrounding area)−average density value (inside of contour)]/[variance (surrounding area)+variance(inside of contour)] (3)

(5) Anatomical Position

Next, the anatomical position of a ROI is recognized. For a chest image, for example, automatic extraction of lung fields, illustrated in FIG. 13B, and bronchial tube, illustrated in FIG. 13D, is performed on an inputted image illustrated in FIG. 13A. Further, interlobar fissures are extracted (FIGS. 13C and 13E) based on the shape of the bronchial tube and lobe classification for classifying the lung fields is performed (upper right lobe, middle right lobe, lower right lobe, upper left lobe, lower left lobe). For more detail information, reference is made to the following documents. A literature "Development of the Procedure for Automatic Extracting Interlobar Fissures and its Performance Evaluation" by T. Hayashi, X. Zhou, T. Hara, H. Fujita, R. Yokoyama, T. kiryu, H. Hoshi, The Institute of Electronics, Information and Communication Engineers (IEICE), Technical Report, MI2003-53, 39-44, 2003 (reference document 1), a literature by Nakada, 15th CADM Meeting, pp 275-276, November, 2005 (reference document 2), a literature by Tanaka, et al., Technical Report of IEICE DII, Vol. J88, pp 1421-1431, April, 2004 (reference document 3), and a literature "ASSERT: a physician-in-the-loop content-based image retrieval system for HRCT image databases" by Shyu C, Brodley C E, Kak A, Kosaka A, Aisen A, and Broderick L, Computer Vision and Image Understanding, 1999; 74: 111-132 (reference document 4), and the like. For example, the anatomical position of the ROI illustrated in FIG. 13A (portion indicated by the black arrow) is recognized as "left lung, upper lobe, S2".

The word/phrase input means 422 replaces corresponding changeable words/phrases included in the report text model with words/phrases describing features of the ROI, such as the shape, size, density, edge state, inside state, anatomical position, and the like, obtained by the feature analysis means 421.

For example, changeable words/phrases in a report text model 130 illustrated in FIG. 14 (words/phrases enclosed by "<" and ">") are replaced by the corresponding words/phrases. In the example illustrated in FIG. 14, the section of "anatomical position" is replaced by <right lung><upper lobe><S2>, the section of "size" is replaced by <25×15 mm>, the section of "shape" is replaced by <near circular shape>, and the section of "edge density" is replaced by <clear edge>. Further, the section of "density" is replaced by <high density>, and the section of "inside state" is replaced by <a cavity> and <involves>.

Next, a report creation flow in the medical system will be described. The method for generating a template for creating a case report is identical to the method described in the first embodiment. Therefore, description will be made of a case where a word/phrase is automatically inputted to a radiological report using CAD function in the report creation support system based on the flowchart illustrated in FIG. 15 here.

First, a doctor performing radiological image reading reads out a diagnosis target image 150 from the image server 3 and displays on the display unit of the work station 4 (S113). Then, the doctor specifies a point C within a pattern which appears to be an abnormal pattern on the displayed diagnosis target image 150 (S114). Then, the extraction means 43 of the report creation support apparatus 40 extracts the abnormal pattern region extending outwardly from the specified point C as a region of interest (ROI) using CAD function (S115).

Then, case images 110 with ROIs similar to the ROI specified on the diagnosis target image 150, which may be identified by ROI position information of the case report creation templates 140 stored in the case report storage unit 7, are retrieved by the similar case image retrieval means 41 (S116).

The feature analysis means 421 of the report creation means 42a analyzes the features, such as the shape, size, density, edge, inside state, anatomical position of the abnormal pattern, and the like from the ROI extracted by the extraction means 43 (S117).

A report text model 130 most appropriate for embedding words/phrases describing the features analyzed by the feature analysis means 421 is selected from report text models 130 of case report creation templates 140 corresponding to the retrieved case images 110 (S118).

The word/phrase input means 422 automatically create a radiological report 120 by replacing changeable words/phrases of the report text model 130 like that shown in FIG. 14 with corresponding words/phrases. The created radiological report 120 of the diagnosis target image 150 is stored in the report server 5 (S119).

Further, an arrangement may be made in which the automatically created radiological report 120 is tentatively displayed to allow the doctor to correct a changeable word/phrase which does not correspond to an actual ROI.

As described in detail, by analyzing the features of a ROI using CAD function, and inputting words/phrases corresponding to the analyzed features to a case report model, a case report may be created automatically without requiring any cumbersome operation.

Further, when a single point within a ROI is specified by a doctor performing radiological image reading, the ROI surrounding the point, such as a tumor or the like, is extracted, so that a report of the region observed by the doctor may be created.

In the embodiment above, the description has been made of a case where a single point on a diagnosis target image is specified first, and then a ROI, such as a tumor or the like, surrounding the point is extracted by the extraction means. Alternatively, a configuration may be adopted in which the ROI is extracted by analyzing the entire region of a diagnosis target image without specifying the point. This allows the report to be created automatically without requiring additional operation of the doctor.

In the embodiment above, the description has been made of a case where a ROI is automatically extracted using CAD function. Alternatively, a configuration may be adopted in which a region of interest position input means 44 is provided, instead of the extraction means 43, in order to accept input of the position of a ROI on a diagnosis target image specified by a doctor performing radiological image reading using a mouse or the like, while observing the diagnosis target image displayed on the display unit, as illustrated in FIG. 16, and the feature analysis means 421 performs feature analysis on the ROI located in the specified position.

In the embodiments described above, the description has been made of a case where case images 100 with ROIs having high similarity levels in features to a ROI of a diagnosis target image 150 are retrieved by the similar case image retrieval means 41 based on the distance of feature amounts in a feature amount space obtained from ROIs, similarity levels obtained by a machine learned through neural network process, and the like. This means that the description has been made of a case where a single search engine (similar case image retrieval means 41) is provided in the embodiments. But, two or more search engines may be provided and used by selecting them according to the disease. This may improve the accuracy since the features appearing on the images differ from disease to disease.

When a doctor performing radiological image reading actually specifies a ROI while observing an image taking on an aspect of disease, it is customary that the doctor prefers to specify a point within an abnormal pattern if it is isolated by clear contour, and prefers to specify an area appearing to be an abnormal pattern by encircling the area if the pattern is extending in dim shade without clear contour, such as a diffuse pattern or the like, so that it is conceivable to change operations according to the pattern.

Figure 17:
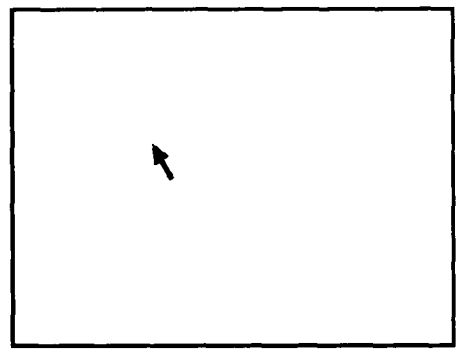
FIG. 17 illustrates an example of specifying operation for a ROI.
Figure 18:
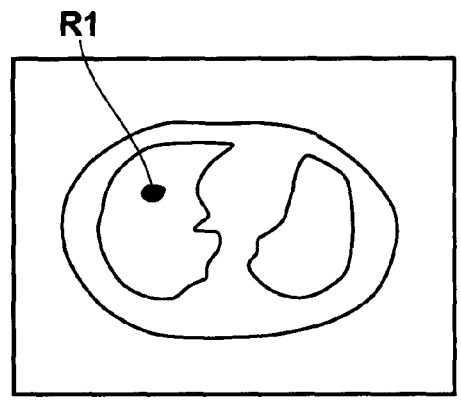
FIG. 18 illustrates the ROI when the operation illustrated in FIG. 17 is performed.

More specifically, for example, an arrangement may be made in which two different types of specifying operations are accepted. The first specifying operation is an operation for specifying one coordinate position on an image by moving the mouse cursor to the position on the image screen and clicking the mouse once on the position as illustrated in FIG. 17. When specifying an isolated pattern R1 as illustrated in FIG. 18 as a ROI, the contour of the isolated pattern R1 is automatically extracted by performing the first specifying operation on the isolated pattern R1 or adjacent area thereof, and the region enclosed by the contour is set as the ROI.

Figure 19:
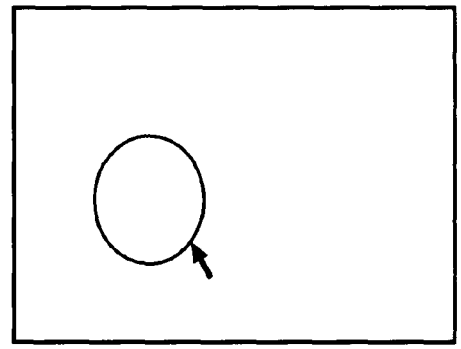
FIG. 19 illustrates another example of specifying operation for a ROI.
Figure 20:
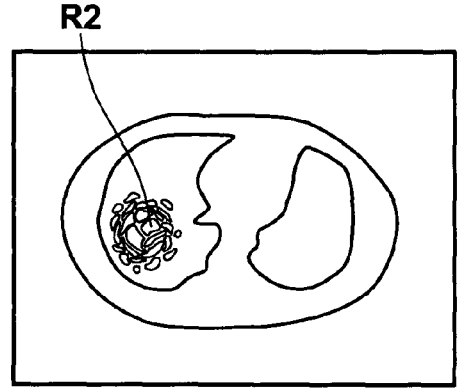
FIG. 20 illustrates the ROI when the operation illustrated in FIG. 19 is performed.

The second specifying operation is an operation for specifying a portion of an image area by moving the mouse cursor to a point of the image screen and dragging the mouse, as illustrated in FIG. 19. In the illustrated example, an ellipsoidal region is specified by the mouse drag, but the region may be specified in rectangular shape. When specifying a diffuse pattern R2 as illustrated in FIG. 20 as a ROI, by specifying a region such that the region encloses the diffuse pattern R2, the specified region is set as the ROI.

As described above, different specifying operations mean that patterns appeared on diagnosis target images are different, which imply that the corresponding diseases are also different. Therefore, a configuration may be adopted in which a selection may be made between a search engine for isolated patterns and a search engine for diffuse patterns according to the specifying operation.

Further, from the combinations of imaged regions and specifying operations, the ROIs may be classified into many different types of diseases. Therefore, a configuration may be adopted in which the search engine is selected according to the combination of the imaged region and specifying operation.

In this way, by selecting the search engine, search accuracy may be improved.

What is claimed is:

1. A report creation support apparatus, comprising:
    a case report storage means for storing a plurality of different case images, each with a report text model associated therewith, the report text model being a text model derived from a report text of the corresponding case image by making at least certain words/phrases included therein changeable;
    a similar case image retrieval means for retrieving a case image which is similar to a diagnosis target image from the case images stored in the case report storage means; and
    a report creation means for creating a report text of the diagnosis target image by accepting input of a word/phrase appropriate for the diagnosis target image in a changeable word/phrase section of the report text model corresponding to the case image which is similar to the diagnosis target image retrieved by the similar case image retrieval means,
    wherein the report text model is generated by a report text model generating device including:
        lexical analysis means for performing lexical analysis on report text associated with the plurality of case images entered in free form text, dividing the text into words, checking the words with a medical dictionary to allocate meanings to the words, and extracting words/phrases describing features of the cases of the case images; and
        report text model generating means for generating report text models in which at least a portion of the extracted words/phrases that describe features of the cases of the case images are changeable;
    wherein the report creation means is a means comprising:
    a feature analysis means for analyzing a feature of a region of interest within the diagnosis target image;
    a word/phrase input means for accepting input of a word/phrase describing the analyzed feature to replace a word/phrase to be replaced therewith among the changeable words/phrases included in the report text model;
    wherein:
    the apparatus further comprises an extraction means for extracting a region of interest from the diagnosis target image; and
    the feature analysis means is a means for analyzing a feature of the extracted region of interest;
    wherein the extraction means is a means for accepting input specifying a single point on the diagnosis target image, and extracting a region of interest located around the single point, and
    wherein the region of interest is extracted by setting a discrimination region that sufficiently includes the region of interest, and by performing evaluation with respect to each pixel along straight lines that pass through each pixel within the discrimination region and a single point with regard to whether it represents an outline.

2. The report creation support apparatus according to claim 1, wherein the feature analysis means is a means for analyzing at least one of the features related to the shape of the region of interest, size of the region of interest, density within the region of interest, density of an edge portion of the region of interest, and anatomical position of the region of interest.

3. The report creation support apparatus according to claim 2, wherein:
    the apparatus further comprises a region of interest position input means for accepting input of a position of a region of interest on the diagnosis target image; and
    the feature analysis means is a means for analyzing a feature of the region of interest located in the inputted position on the diagnosis target image.

4. The report creation support apparatus according to claim 2, wherein:
    the apparatus further comprises an extraction means for extracting a region of interest from the diagnosis target image; and
    the feature analysis means is a means for analyzing a feature of the extracted region of interest.

5. The report creation support apparatus according to claim 4, wherein:
    the apparatus further comprises a region of interest position input means for accepting input of a position of a region of interest on the diagnosis target image; and
    the feature analysis means is a means for analyzing a feature of the region of interest located in the inputted position on the diagnosis target image.

6. The report creation support apparatus according to claim 1, wherein the region of interest is a tumor region.

7. A report creation support method, comprising:
    a lexical analysis step for performing a lexical analysis on a report text stored in association with each of a plurality of different case images in a case storage means;
    a report text model generation step for generating a report text model by extracting words/phrases describing features of the case of the case image from the words/phrases obtained through the lexical analysis, and making at least certain words/phrases of the extracted words/phrases changeable;
    a case report storing step for storing the generated report text model in association with each of the plurality of corresponding case images in a case report storage means;

a similar case retrieval step for retrieving a case image which is similar to a diagnosis target image from the case images stored in the case report storage means; and a report text model output step for outputting a report text model corresponding to the retrieved case image which is similar to the diagnosis target image, wherein the report text model is generated by a report text model generating device including:

lexical analysis means for performing lexical analysis on report text associated with the plurality of case images entered in free form text, dividing the text into words, checking the words with a medical dictionary to allocate meanings to the words, and extracting words/phrases describing features of the cases of the case images; and report text model generating means for generating report text models in which at least a portion of the extracted words/phrases that describe features of the cases of the case images are changeable;

wherein the report creation support method further comprises:

a feature analysis step for analyzing a feature of a region of interest within the diagnosis target image;

a word/phrase input step for accepting input of a word/phrase describing the analyzed feature to replace a word/phrase to be replaced therewith among the changeable words/phrases included in the report text model;

an extraction step for extracting a region of interest from the diagnosis target image; and wherein the feature analysis step is for analyzing a feature of the extracted region of interest;

wherein the extraction step is for accepting input specifying a single point on the diagnosis target image, and extracting a region of interest located around the single point, and wherein the region of interest is extracted by setting a discrimination region that sufficiently includes the region of interest, and by performing evaluation with respect to each pixel along straight lines that pass through each pixel within the discrimination region and a single point with regard to whether it represents an outline.

8. A non-transitory computer readable storage medium storing a program for causing a computer to function as:

a similar case image retrieval means for retrieving a case image which is similar to a diagnosis target image from a plurality of different case images, each stored with a report text model associated therewith in a case report storage means, the report text model being a text model derived from a report text of the corresponding case image by making at least certain words/phrases included therein changeable; and a report creation means for creating a report text of the diagnosis target image by accepting input of a word/phrase appropriate for the diagnosis target image in a changeable word/phrase section of the report text model corresponding to the case image which is similar to the diagnosis target image retrieved by the similar case image retrieval means, wherein the report text model is generated by a report text model generating device including:

lexical analysis means for performing lexical analysis on report text associated with the plurality of case images entered in free form text, dividing the text into words, checking the words with a medical dictionary to allocate meanings to the words, and extracting words/phrases describing features of the cases of the case images; and report text model generating means for generating report text models in which at least a portion of the extracted words/phrases that describe features of the cases of the case images are changeable;

wherein the report creation means is a means comprising:

a feature analysis means for analyzing a feature of a region of interest within the diagnosis target image;

a word/phrase input means for accepting input of a word/phrase describing the analyzed feature to replace a word/phrase to be replaced therewith among the changeable words/phrases included in the report text model;

wherein:

the apparatus further comprises an extraction means for extracting a region of interest from the diagnosis target image; and the feature analysis means is a means for analyzing a feature of the extracted region of interest;

wherein the extraction means is a means for accepting input specifying a single point on the diagnosis target image, and extracting a region of interest located around the single point, and wherein the region of interest is extracted by setting a discrimination region that sufficiently includes the region of interest, and by performing evaluation with respect to each pixel along straight lines that pass through each pixel within the discrimination region and a single point with regard to whether it represents an outline.

* * * * *